United States Patent
Hoag et al.

(10) Patent No.: US 11,134,689 B2
(45) Date of Patent: Oct. 5, 2021

(54) NATURAL VOLATILE PLANT OILS TO REPEL ARTHROPODS

(71) Applicant: Shepard Farms, LLC, South Windsor, CT (US)

(72) Inventors: George E. Hoag, South Windsor, CT (US); Douglas K. Anderson, South Windsor, CT (US)

(73) Assignee: Shepard Farms, LLC, South Windsor, CT (US)

( * ) Notice: Subject to any disclaimer, the term of this patent is extended or adjusted under 35 U.S.C. 154(b) by 0 days.

(21) Appl. No.: 14/353,764

(22) PCT Filed: Oct. 26, 2012

(86) PCT No.: PCT/US2012/062319
§ 371 (c)(1),
(2) Date: Apr. 23, 2014

(87) PCT Pub. No.: WO2013/063534
PCT Pub. Date: May 2, 2013

(65) Prior Publication Data
US 2014/0335140 A1 Nov. 13, 2014

Related U.S. Application Data

(60) Provisional application No. 61/552,488, filed on Oct. 28, 2011.

(51) Int. Cl.

| | |
|---|---|
| *A01N 65/44* | (2009.01) |
| *A01N 25/18* | (2006.01) |
| *A01N 25/02* | (2006.01) |
| *A01N 25/34* | (2006.01) |
| *A01N 27/00* | (2006.01) |
| *A01N 31/02* | (2006.01) |
| *A01N 65/22* | (2009.01) |
| *A01N 65/24* | (2009.01) |
| *A01N 65/26* | (2009.01) |
| *A01N 65/28* | (2009.01) |
| *A61K 31/01* | (2006.01) |
| *A61K 36/53* | (2006.01) |
| *A61K 36/534* | (2006.01) |
| *A61K 36/58* | (2006.01) |
| *A61K 36/61* | (2006.01) |
| *A61K 36/899* | (2006.01) |
| *A61K 47/02* | (2006.01) |
| *A61K 47/46* | (2006.01) |

(52) U.S. Cl.
CPC ............ *A01N 65/44* (2013.01); *A01N 25/02* (2013.01); *A01N 25/18* (2013.01); *A01N 25/34* (2013.01); *A01N 27/00* (2013.01); *A01N 31/02* (2013.01); *A01N 65/22* (2013.01); *A01N 65/24* (2013.01); *A01N 65/26* (2013.01); *A01N 65/28* (2013.01); *A61K 31/01* (2013.01); *A61K 36/53* (2013.01); *A61K 36/534* (2013.01); *A61K 36/58* (2013.01); *A61K 36/61* (2013.01); *A61K 36/899* (2013.01); *A61K 47/02* (2013.01); *A61K 47/46* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 5,230,894 A | 7/1993 | Robert et al. | |
| 6,936,269 B2 | 8/2005 | Robinson | |
| 2002/0044968 A1 | 4/2002 | van Lengerich | |
| 2004/0031191 A1* | 2/2004 | D'Amico | A61L 9/013 44/275 |
| 2004/0142010 A1* | 7/2004 | Maravelis | 424/405 |
| 2004/0241195 A1 | 12/2004 | Tollens | |
| 2005/0019432 A1* | 1/2005 | Baker | A01N 65/00 424/739 |
| 2005/0214337 A1 | 9/2005 | McGee et al. | |
| 2006/0251743 A1 | 11/2006 | Karita | |
| 2006/0257443 A1 | 11/2006 | Johal | |
| 2008/0193387 A1 | 8/2008 | De Wolff | |
| 2008/0213408 A1 | 9/2008 | Baker et al. | |
| 2011/0183017 A1 | 7/2011 | Darling | |

FOREIGN PATENT DOCUMENTS

| | | | |
|---|---|---|---|
| FR | 2778095 A1 | | 11/1999 |
| JP | H0576597 A | | 3/1993 |
| JP | 08053305 | | 2/1996 |
| JP | 2000281505 A | * | 10/2000 |
| JP | 2003267466 A | * | 9/2003 |
| WO | 0021364 A2 | | 4/2000 |
| WO | 0145504 A2 | | 6/2001 |
| WO | WO 03-051112 A1 | | 6/2003 |

OTHER PUBLICATIONS

Supplementary European Search Report dated Mar. 9, 2015 (EP 12843423.0).
International Search Report and Written Opinion for Application No. PCT/US2012/062319 dated Feb. 28, 2013.
European Patent Office Communication dated Aug. 23, 2017 (European Patent Application No. 12843423.0).
Abu Bakr Mohammad.Bin Zakariyya Al-Razi, Kitaab-al-Haawi-fil-Tibb, vol. XXI Part I (9th century AD), 04 (p. 04-07) ( Ref.pg. No. of publication:245 ), 1968 AD, Dayerah-al- Ma'aarif ,Usmania, Hyderabad, India.†

(Continued)

*Primary Examiner* — Terry A McKelvey
*Assistant Examiner* — Catheryne Chen
(74) *Attorney, Agent, or Firm* — Alix, Yale & Ristas, LLP

(57) ABSTRACT

A composition and method for the controlled release of natural plant oils (essential oils) from a wax matrix to repel insects, arachnids, and other arthropods.

33 Claims, 10 Drawing Sheets

(56) References Cited

OTHER PUBLICATIONS

Mohammad Najmul Ghani Khan, Khazaain-al-Advia, vol. III (20th century AD), 06 (p. 08-13) ( Ref.pg. No. of publication:995 ), 1926 AD, Nadeem Yunus Printer / Sheikh Mohd Basheer & Sons, Lahore.†

Mohammad Najmul Ghani Khan, Qaraabaadeen Najm-al-Ghani (20th century AD), 04 (p. 14-17) ( Ref.pg. No. of publication: 165 ), 1928 AD, Munshi Nawal Kishore, Lucknow, India.†

\* cited by examiner
† cited by third party

Figure 1. Fiber Mesh Support with 5 mm Open Mesh Size
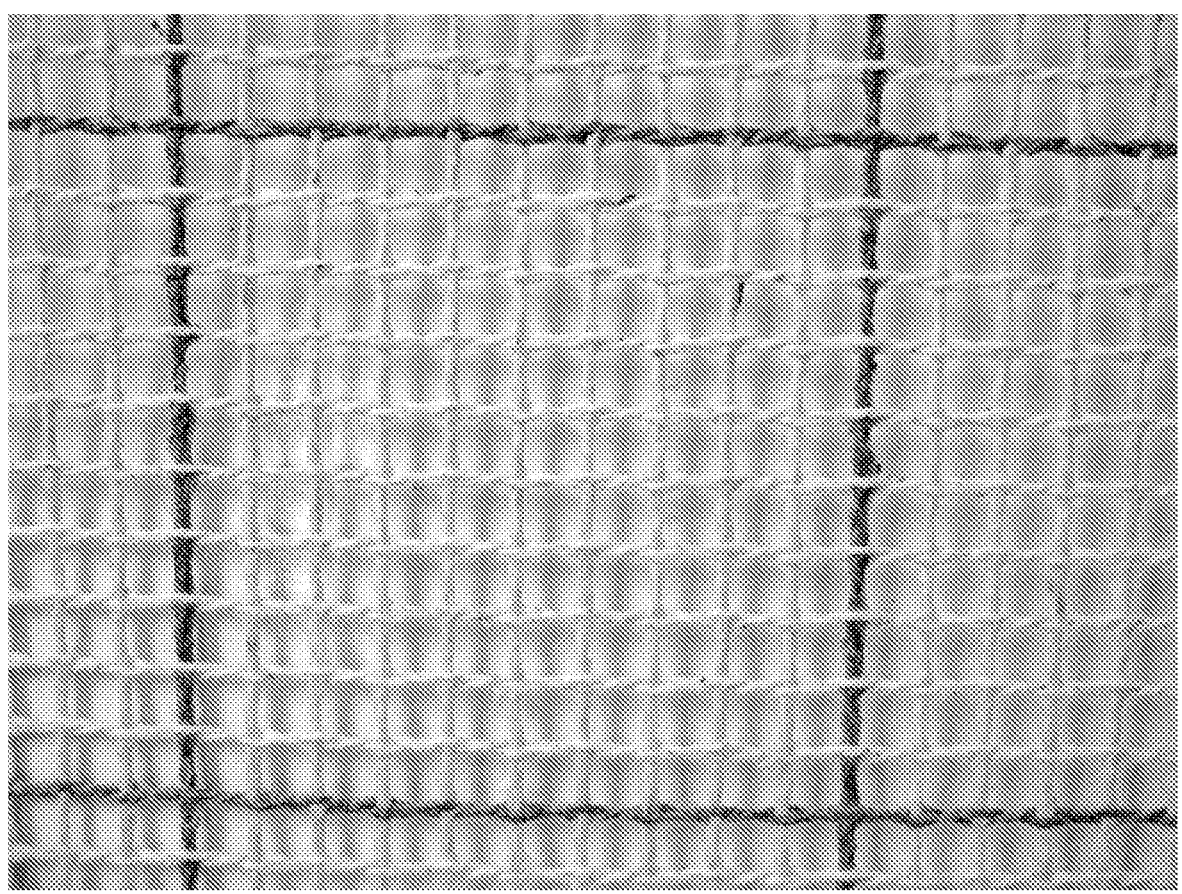

Figure 2. Spiral Wound Mesh Support Material
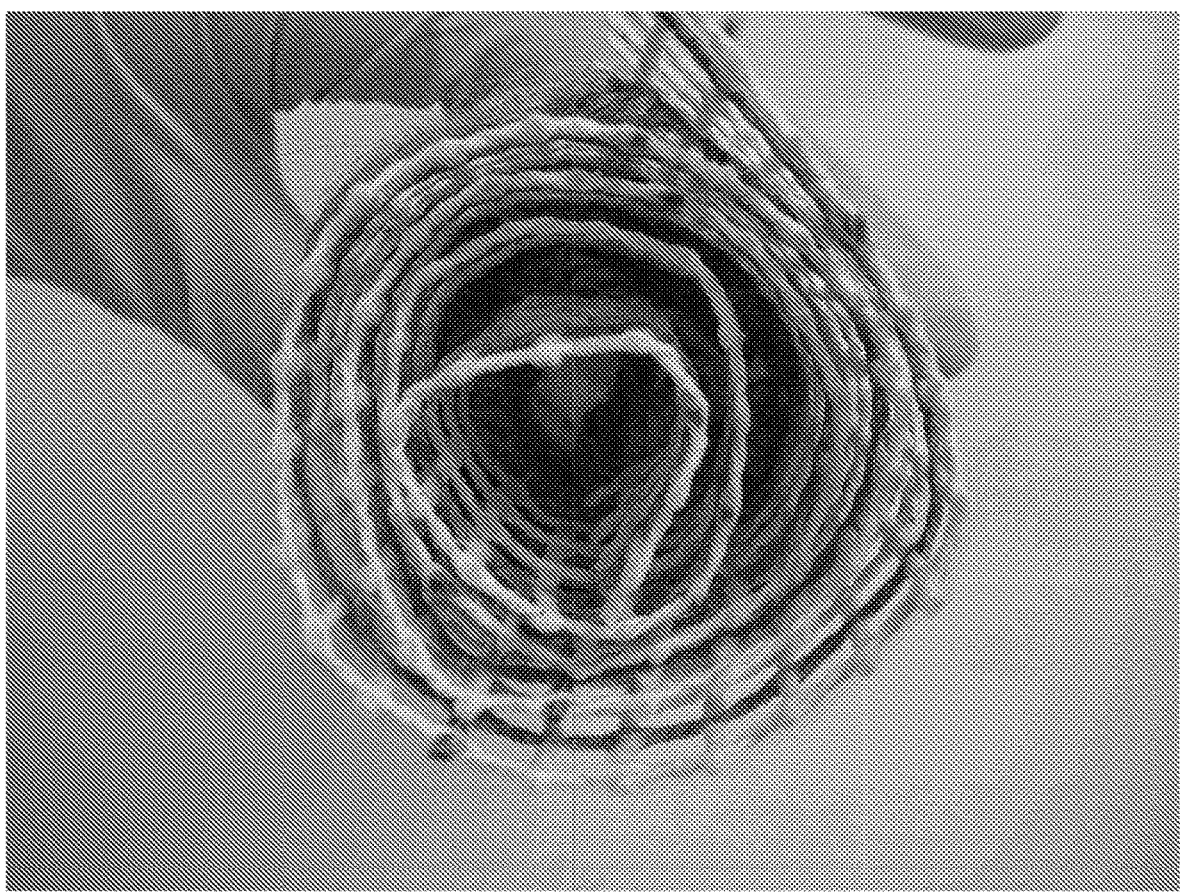

Figure 3. Spiral Wound Mesh Support Material
Inside a Highly Pervious Plastic Support Housing
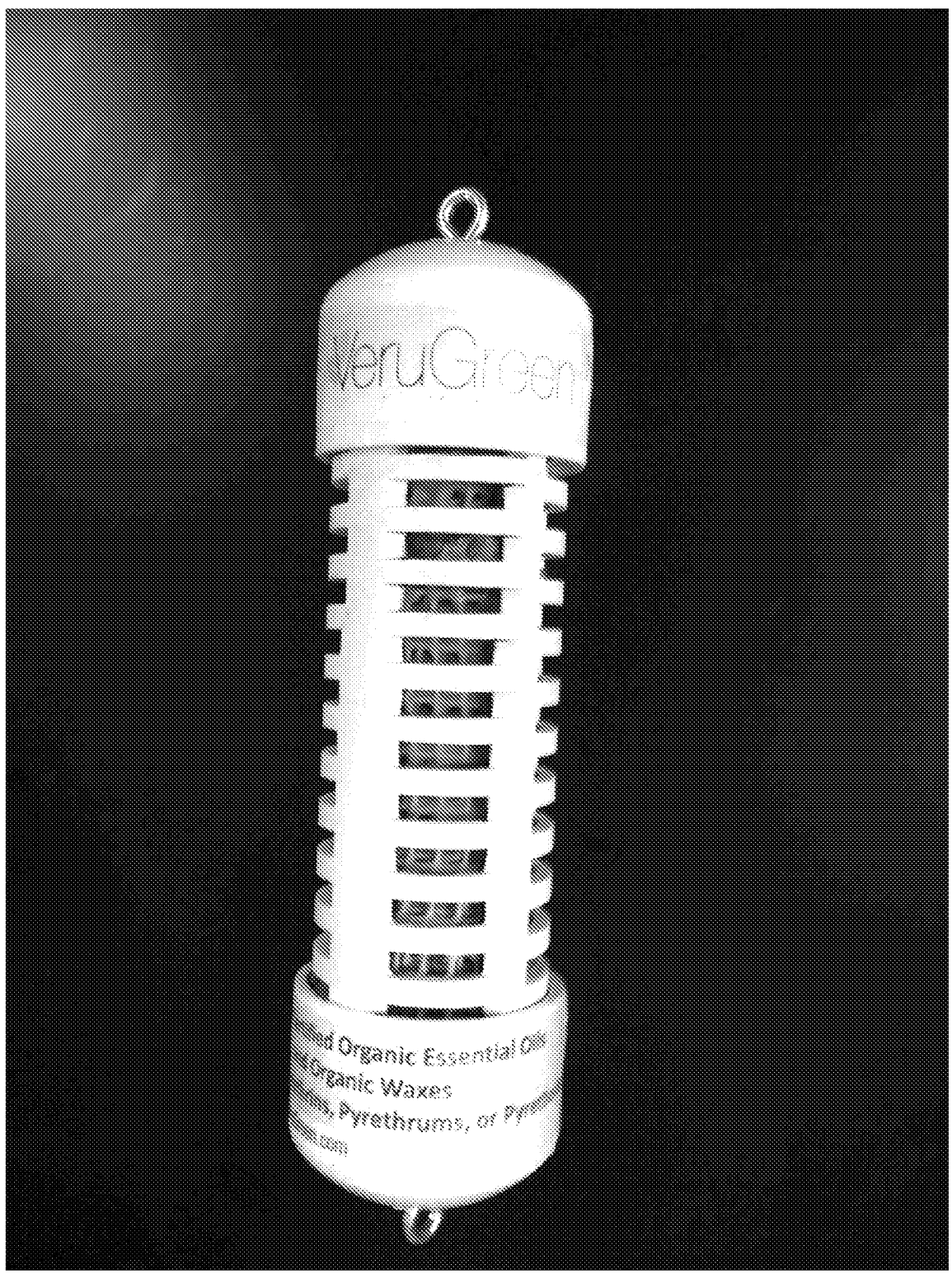

Figure 4. Spiral Wound Mesh Support Material
Inside a Moderately Pervious Plastic Support Housing
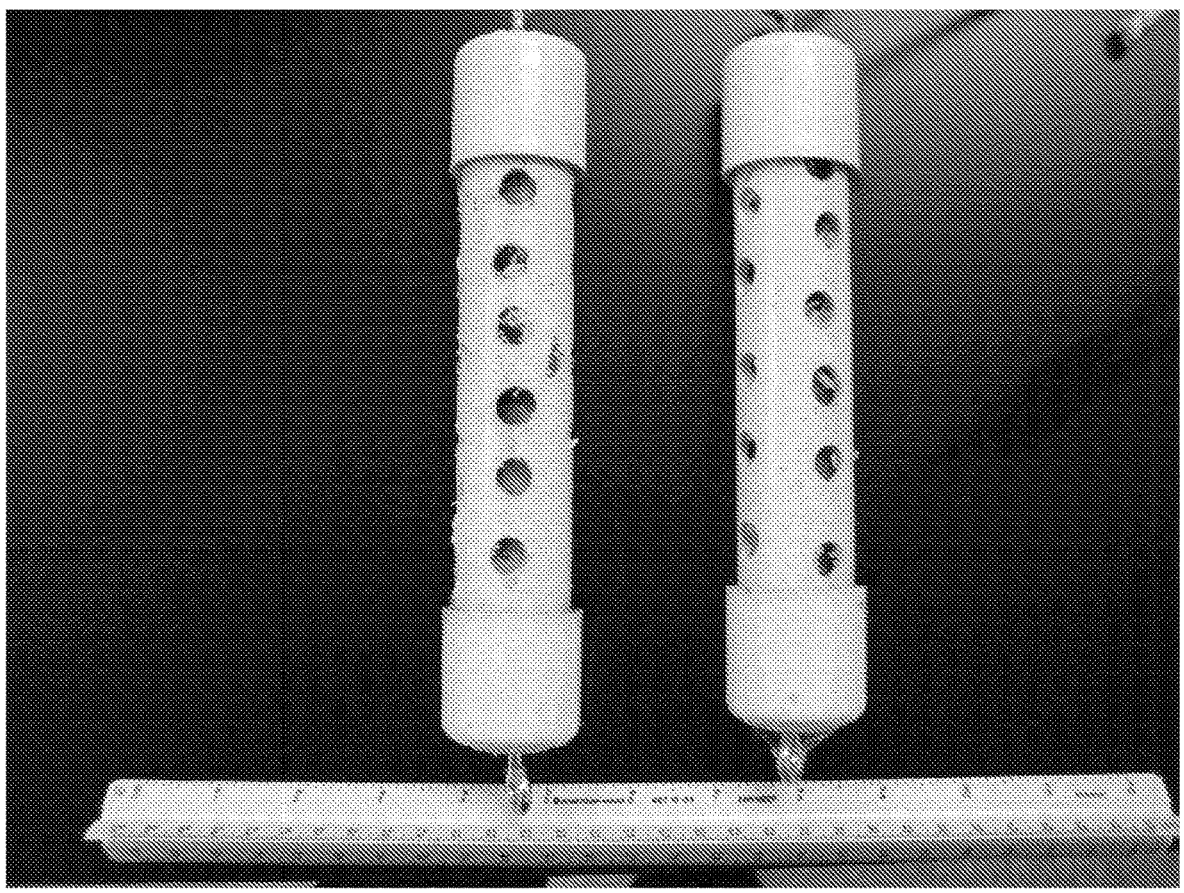

Figure 5A. Wax Coated Support Material
Following Four Months of Deployment
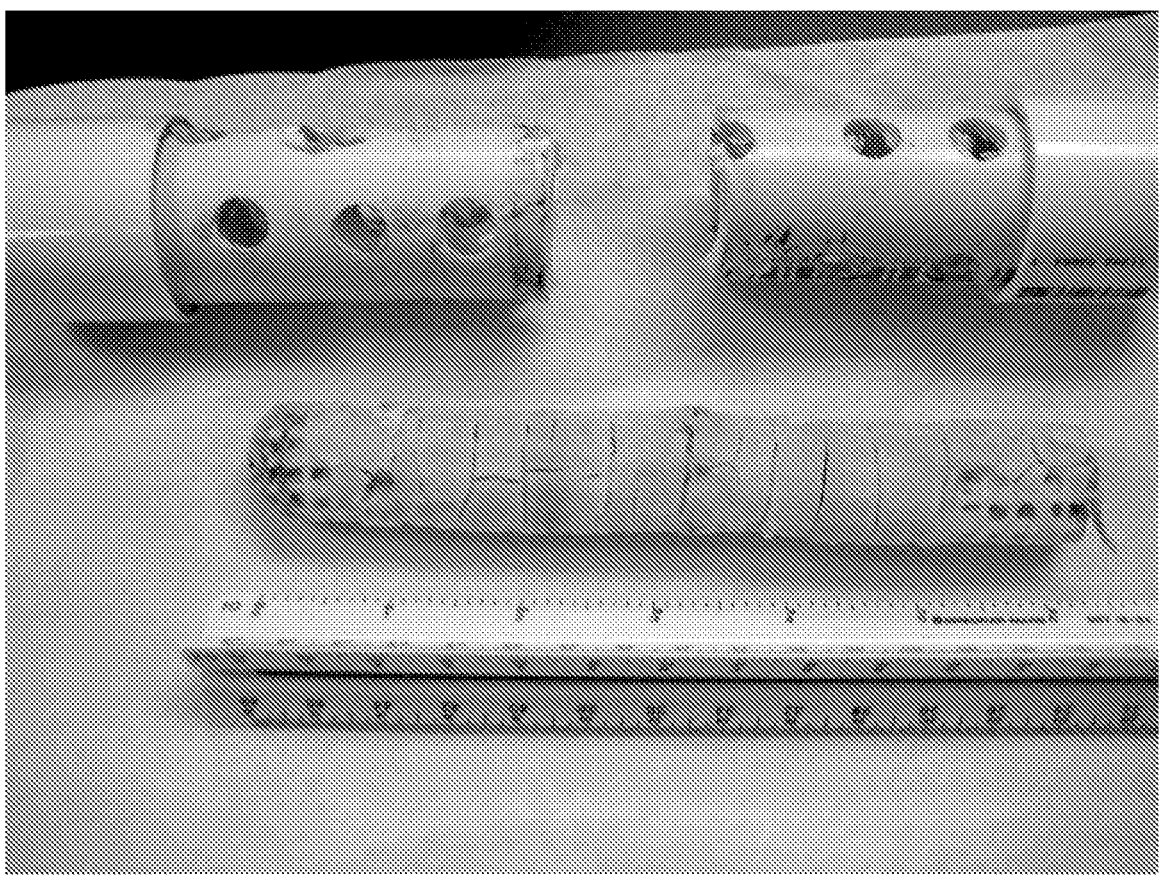

Figure 5B. Polypropylene Injected Molded Essential Oil-Wax Matrix Housing
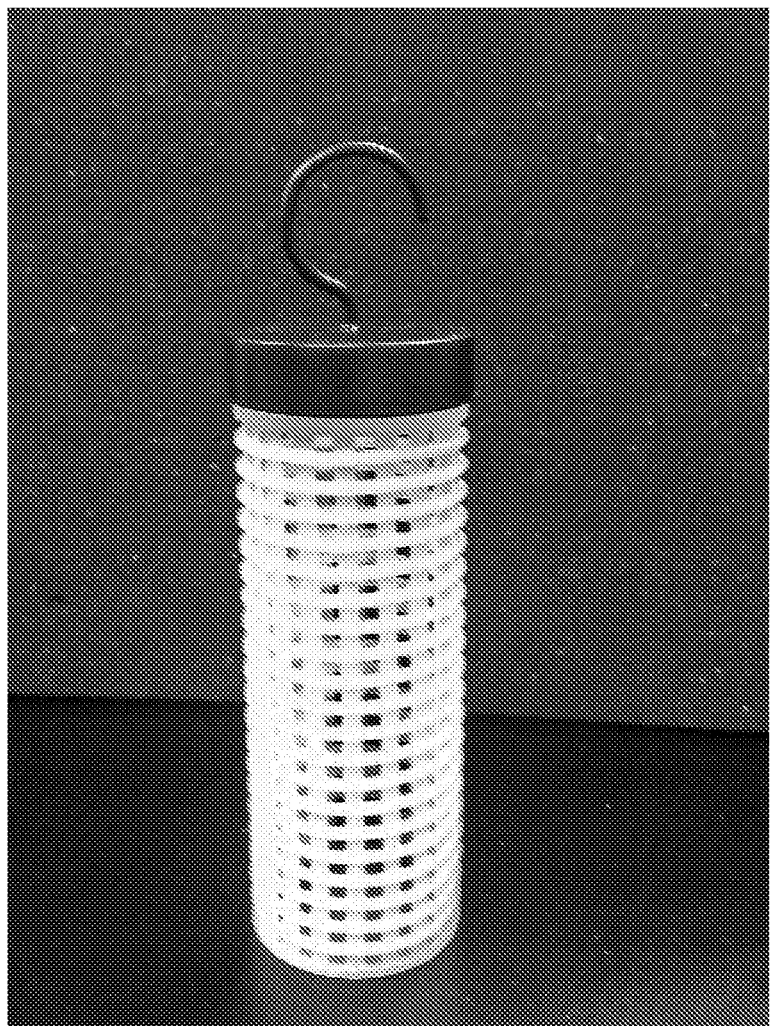

Figure 6. Polypropylene Pellets Coated with Essential Oil-Wax Matrix

Figure 7. Injected Molded Housing with Essential Oil-Wax Matrix Coating Polypropylene Plastic Pellets
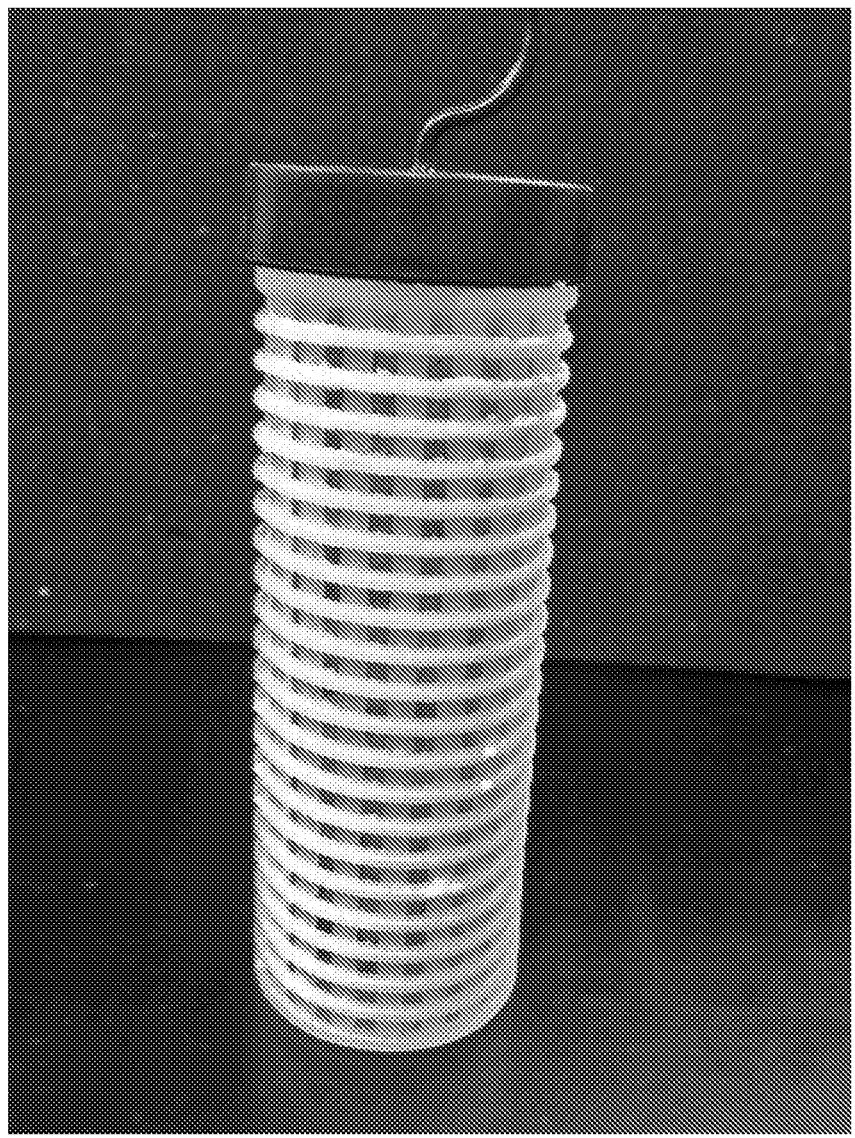

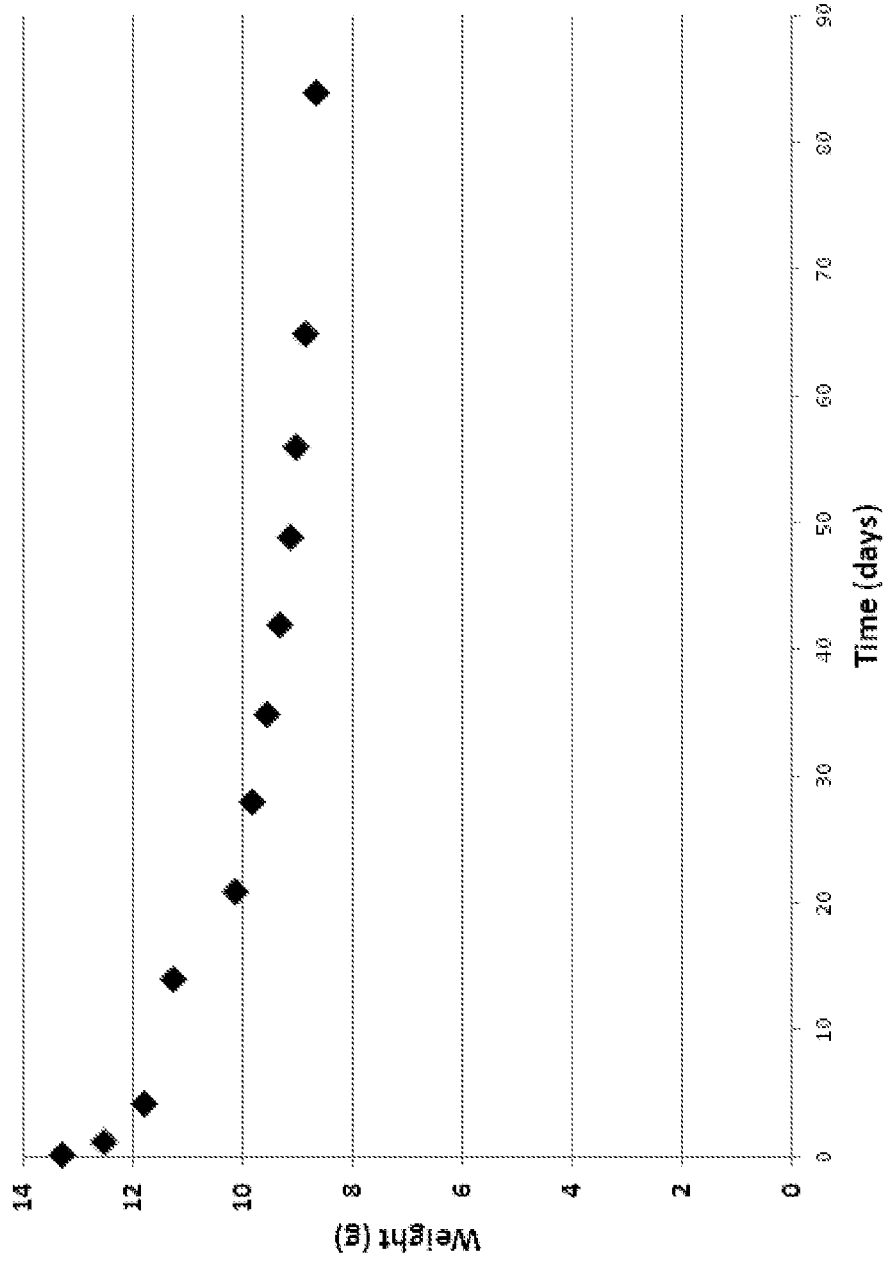

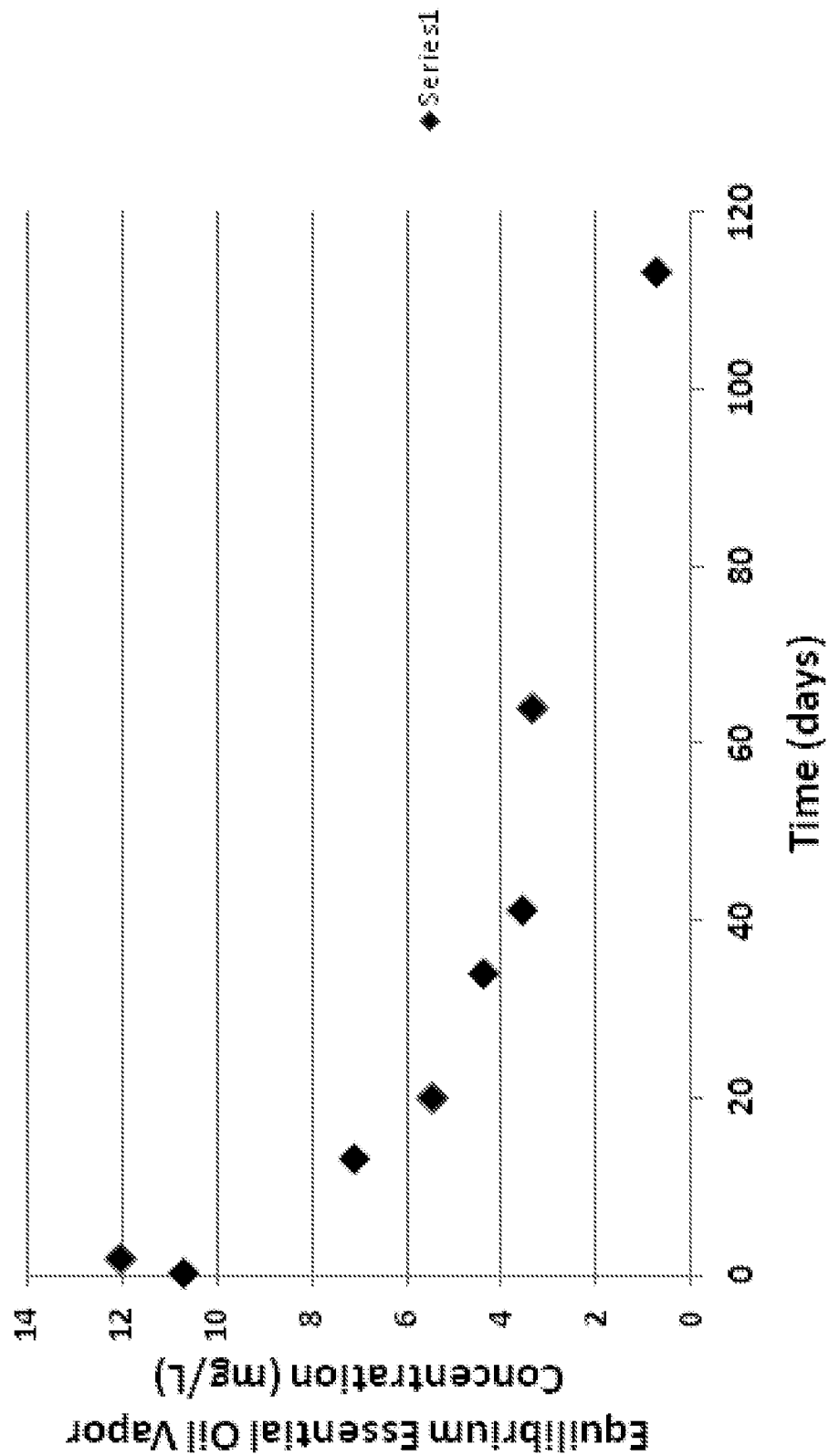

NATURAL VOLATILE PLANT OILS TO REPEL ARTHROPODS

SUMMARY

This application involves a composition and method for the slow release of natural plant oils from a wax matrix to repel insects, arachnids and other arthropods. In this invention all organic grade materials can be used as alternative to those synthetic and highly toxic chemicals typically used such as DEET (N,N-diethyl toluamide), permethrin, d-phenothrin, etofenprox, fipronil, imidacloprid, ethyl hexanediol and other pyrethroid chemicals. While the ability of natural plants oils, particularly essential oils to repel flying, crawling and other insects, including larval stages, arachnids and other arthropods is well known, typically these oils are either mixed with fixed oils for topical use or mixed in water with surfactants for use in spray applications. By controlling the selection and concentration of specific essential oils used in the oil portion of the composition, the rheology of the wax matrix by the use of waxes with various properties and by varying the oil to wax ratio, a variety of essential oil in wax compositions can be manufactured. Varying the composition of the oil, the oil to wax ratio and the type of wax used enables control of the essential oil volatilization rate into the gas phase. The rate of volatilization of the essential oil volatile fraction into the gas phase controls the effectiveness of repellency of the device to insects. The creation of an essential oil-wax composition allows for a method of long-term evaporation and release of the volatile essential oil components into a gas phase, such as into the ambient air or into a flowing air stream associated with air handling or air circulation equipment. Various housings and materials can be used to contain the essential oil wax matrix, with specified properties vapor diffusion and air permeability to further control the rate of volatilization from the essential oil-wax matrix into the ambient air. While the primary application of this invention is to repel insects from their nuisance to people, animals and food and use in buildings, enclosed spaces, semi-enclosed spaces or outdoors, additional uses can be for aromatherapy and medical therapy for people and animals. The controlled release or a fragrance into the air is also possible with the essential oil-wax matrix composition.

Control of flying insect repellency and insecticidal activity in the agricultural industry is important in the control of disease vectors, wound management, bacterial and fungal infection prevention and the overall comfort and well being of animals and people associated with animal care. High density agricultural facilities for animal production that involve confined or semi-confined spaces require flying and crawling insect control. Additionally, control of pests in crops grown in confined or semi-confined spaces such as greenhouses and hydroponic facilities is an essential management practice to ensure high quality production. Bacterial and fungal infection control of animals and agricultural plant crops is an important factor in production. Toxic chemicals are typically used in agricultural production to control flying and crawling insects and their larval stages, as well as for bacterial and fungal control.

With the widespread public and government concern regarding the toxicity of synthetic pesticides and insect repellents, there is currently great interest in the development and use of bioinsecticides, botanical insecticides and repellents. The Food Quality Protection Act of 1996 in the United States which amended prior pesticide legislation was developed to establish a more consistent and protective regulatory scheme with health-based standards for all pesticides in all foods. It also provides special protections for infants and children and expedites approval of safer pesticides. It also provides for periodic re-evaluation of pesticide registrations and tolerances to ensure that the scientific data supporting pesticide registrations will remain up to date.

Plant materials and plant oils have been used for thousands of years to repel insects and for medicinal purposes. The recorded use of plant materials and plant oils can be dated back to Egyptian periods, including in the remedy called Kyphi, dedicated to the goddess Isis (Manniche (1989)). Recipes for Kyphi are found on the temple walls at Edfu and Philae and documented by Plutarch. Bado et al., (2004) reported that many species in the plant kingdom synthesize a variety of secondary plant metabolites which play a role in their defense against arthropods. In a review article, Isman (2000) cites that "Recent investigations in several countries confirm that some plant essential oils not only repel insects, but have contact and fumigant insecticidal actions against specific pests, and fungicidal actions against some important plant pathogens. Additionally, essential oils are reported to be animal attractants and repellents. Baser and Buchbauer (2010) summarize repellency of essential oil matrices to dogs and cites several U.S. patents claiming as such. Kambouzia et al., (2009) extracted Eucalyptus oil from the plant *Eucalyptus leucoxylon* and demonstrated toxicity to three stored product insects (*Callosobruchus maculatus, Sitophilus oryzae* and *Tribolium castaneum*) that were exposed to gas phase concentrations of the extracts. In this study by Kambouzia et al., (2009) mortality of 1 to 7 day old adult insects was observed with oil dosed on filter paper to yield gas phase concentrations varying from 37 µg/L to 370 µg/L. The insecticidal activity of *Eucalyptus globulus* (Mirtaceaea) essential oil was tested by Marreggiani (2008) with *Aphis gossypii* (*Hemiptera*, Aphididae) adults. The $LC_{50}$ values of acetone diluted *Eucalyptus* oil placed at various concentrations on filter paper on Petri dishes then sealed with adult insects were 1,950 ppm, 2000 ppm and 2000 ppm, at 2, 4 and 6 hours contact times, respectively. They confirmed the major component in the *Eucalyptus* oil was 1-8 cineole and that their work, in conjunction with others, could be a good basis for the development of more environmentally safe agricultural insecticides. Clemente, et al., (2006) reported high insecticidal activity of 1,8-cineole against the fruit fly (*Ceratitis capitata*). Antifungal activity of eucalyptus essential oil was reported by Katooli, et al. (2011) for complete growth inhibition of *Pythium ultimum* and *Rhizoctonia solani* for 30 days following treatment. In this study by Katooli, et al. (2011) Bipolaris sorokiniana and *Callectotrichum gloeosporoides* growth was inhibited for 5 days following treatment and *Aspergillus flavus* showed no growth inhibition after 3 days.

Recent monographs on essential oil safety (Tisserand and Balacs 1995) and the chemistry, biochemistry, production and properties of essential oils (Baser and Buchbauer) clearly indicate that certain essential oils can be safely used for many applications. While essential oils generally consist of hundreds of individual compounds, many essential oils contain one or two compounds that provide for its specific properties. The classes of compounds found in essential oils include hydrocarbons, such as terpenes and oxygenated compounds, such as alcohols, aldehydes, ketones, esters, phenols, acids and furans. The volatile compounds in plant biological essential oils include mono- and sesquiterpenoids, benzenoids, and phenylpropanoids. Additionally, alcohols, aldehydes, ketones, esters, phenols, ethers and oxides, peroxides, furans, lactones and acids can be found in certain essential oils. The major chemical constituents in essential oils from specific plants are known, despite the fact that hundreds of compounds comprise the essential oils.

BRIEF DESCRIPTION OF THE DRAWINGS

FIG. 1 shows a polyester/cotton fiber mesh material.
FIG. 2 shows a spirally wound mesh fabric.
FIG. 3 shows a plastic housing containing an essential oil wax matrix on a supported mesh fabric.
FIG. 4 shows units according to the invention.
FIG. 5A shows a wax coated support material.
FIG. 5B shows an essential oil-wax coated mesh.
FIG. 6 shows an essential oil-wax matrix.
FIG. 7 shows an injection molded housing containing essential oil-wax matrix coated polypropylene particles.
FIG. 8 shows results of testing.
FIG. 9 shows results of GC/MS analysis.

DETAILED DESCRIPTION OF THE INVENTION

The method of manufacturing the essential oil-wax matrix consists of selecting one or more essential oil components for the formulation and one or more wax components and mixing together during heating sufficient to melt the wax. A list of essential oils and their major constituent components that are preferred for use in this invention are listed in Table 1. The most preferred composition of the essential oil-wax matrix is listed in Table 2. The wax can be melted separately before the essential oils are added or after the essential oils and solid wax are added. Melting the wax prior to addition of the essential oils can reduce the volatilization of the essential oils while the temperatures of the essential oils are elevated. The melted wax-essential oil mixture is then either sorbed onto a porous or solid material, such as wood pellets or alternatively onto a mesh, then allowed to solidify. Alternatively, the melted wax-essential oil mixture can be solidified into a solid mass. The melted essential oil-wax matrix can also be solidified into a foam or a porous plastic material. The melted essential oil-wax matrix can also be infused into or solidified onto natural or synthetic materials including sponge-like materials, metals, wood, fibers, strings, ropes and cloths. The melted essential oil-wax matrix can also be used to infuse into or solidify onto certain geologic materials, such as pumice, gravel, sand, stone and clays. Additionally, the melted essential oil wax matrix can be used to infuse into or sorb onto, natural or manufactured materials such as, zeolites, resins and granular activated carbon. A person ordinarily skilled in the art would recognize that there are many ways to heat the essential oils and waxes and mixtures thereof, including gas and electric, convection, microwave, tube heaters, heat exchangers, oil baths and solar heaters. A person ordinarily skilled in the art would recognize that there are many types of support substrates that the melted wax-essential oil matrix could be sorbed or solidified onto to enable transfer from the wax-essential oil matrix into a gas phase. Additionally, the choice of the wax used can be selected based on the ambient temperature of the environment in which the essential oil-wax matrix is to be used to ensure that the wax will not melt in the specific environment in which the invention is to be used.

In this invention, the controlled volatilization of essential oils from the essential oil-wax matrix is not only controlled by the composition of the essential oils, the oil to wax ratio and the type and rheology of the waxes used but also the surface area of the essential oil-wax matrix exposed to a gas phase, whether it be ambient air, air in an enclosed or semi-enclosed space, or in an advectively flowing air associated with air handling and air management systems. The three major variables that contribute to the mass flux of essential oil volatilization are as follows:

the rate of essential oil volatilization controlled by the composition of the essential oil-wax matrix; and
the surface area to gas ratio of the essential oil wax matrix and the total surface area exposed to a gas phase
the gas permeability, the diffusivity or the void-to solid ratio of the housing in which the essential oil wax matrix is placed In one embodiment of this invention, the melted essential oil-wax matrix is placed on a support material and the melted essential oil-wax matrix is allowed to solidify. The support material can be a synthetic or natural material composition and can be fibers, solid particles or engineered or natural particles with high surface area to volume ratios.

The essential oil-wax composition can be manufactured from many waxes and essential oils. Preferred waxes are candilla wax, beeswax and carnauba wax. These are inexpensive waxes that can be combined to control the rheology of the wax-essential oil matrix. Candilla wax is the most preferred wax in this invention. It is important to control the melting point of the wax matrix to insure that the melting point is significantly greater that the ambient temperature in which the essential oil-wax matrix will be place to avoid melting of the matrix.

Many essential oils are reported in the literature to have insect repellent properties for horses by Faith (2002), as follows:

Cajeput, Eucalyptus, Eucalyptus Peppermint, Geranium, Lemon, Lemongrass, Long Leaf Pine, Peppermint, Sandalwood, Tea Tree, Citronella, Eucalyptus Lemon, Garlic, Lavender, Lemon Balm, Litsea cubeba, Patchouli, Rosemary, Scotch Pine and Virginia Cedarwood.

EXAMPLES

An example of one way the surface area of the essential oil-wax matrix exposed to a gas phase can be increased in this invention is to place spirally wound rolled mesh fabric (1.5 mm diameter polyester/cotton fabric string) with a 5 mm×5 mm open space mesh into a bath of melted essential oil-wax and then allowing a specified mass of the essential oil-wax matrix to solidify onto the mesh fabric. The polyester/cotton fiber mesh material used in this example is shown in FIG. 1. An end view of a spirally wound mesh fabric is shown in FIG. 2. A person ordinarily skilled in the art would readily recognize that many fabrics and geometries of mesh type fabrics could be used as support material for the essential oil-wax matrix.

Controlling the mass of wax that is solidified onto the mesh fabric enables control of the dimensions of the open mesh space remaining after the wax is solidified. This approach enables control of the permeability to air of the mesh supported essential oil-wax matrix. Independent variables that can be controlled to affect the rate of essential oil volatilization from the essential oil-wax matrix include the mesh material opening dimensions, the open mesh area surface area and the total surface area of the mesh support. The mesh material can be rolled into a spiral with spacers to minimize the mesh surfaces from contacting one another when in the spiral form. The emplacement of the mesh in a spiral configuration is one way to increase the surface area of the mesh that can be placed in a given geometry. The melted essential oil-wax mixture is placed into a container and the spirally wound mesh is alternatively dipped into the melted essential oil-wax matrix and raised out of the container to cool. Once the spirally wound mesh support material is cooled with the specific and desired mass of essential oil-wax matrix on the mesh support, the composition can be placed inside a support housing, such as perforated plastic, metal, or porous natural or engineered materials. It is desirable for the support housing to be constructed such that it also has an controllable and specified air permeability to enable air to flow through the housing containing the essential oil-wax matrix, enabling mass transfer and diffusion of essential oils into the gas phase to pass through the housing and into the gas phase of the confined, semi-confined, indoor or outdoor space. An example of a plastic housing containing an essential oil wax matrix on a supported mesh fabric is shown in FIG. 3. The plastic material used is a 2 inch (5.1 cm) diameter slotted PVC Schedule 40 pipe with 0.25 inch (0.60 cm) wide by 0.875 inch (2.2 cm) long perforations. The 8 inch (20.3 cm) long PVC pipe is slotted to provide a 29% open area. The total open area of the 2 inch (0.60 cm) diameter 8 inch (20.3 cm) long perforated pipe shown in FIG. 3 is 94.9 $cm^2$. The PVC pipe is capped and threaded eye bolts are placed on each end to hang in an enclosed, semi-enclosed or open space. Persons ordinarily skilled in the art will recognize that many types of natural and synthetic mesh materials, particles, fabric, solids, and engineered housing materials that are spherical, circular, rectangular, cubical, cylindrical particles and surfaces or of other geometries can be used to support or enclose the essential oil-wax matrix. Materials and fabrics pervious to gases but not to liquids also can be used as housing materials. Gore-Tex is an example of such a material.

Another embodiment of this invention includes a method of solidifying the essential oil wax matrix onto common gas-liquid exchange materials, such as Jaeger TriPaks®, Jaeger Metal MaxPaks™, Jaeger Rashig SuperPaks, Jaeger Rings and Saddles and other types of gas-liquid exchange materials. Packings containing gas-liquid exchange materials can be coated with the essential oil-wax matrix and be used to transfer essential oils in a controlled manner into an advectively flowing gas phase, or by diffusion into a gas phase. The advectively flowing gas phase can be induced in an engineered air handling system or naturally present in a building, a semi-confined space or the open air. These packing materials coated with an essential oil-wax matrix can be placed in line into air handling systems that supply air to agricultural facilities, medical or veterinarian treatment facilities and other types of enclosed or semi-enclosed spaces. A person ordinarily skilled in the art would readily recognize that other types of filtration and support surfaces could be coated with the essential oil-wax matrix and be subsequently used in an air handling, air management or air treatment system.

Another preferred embodiment of the invention is to use a natural wood pellets as a sorbent packing material for the oil-wax matrix. The preferred wood pellets are Southern Yellow Pine or bamboo pellets, but other types of plant biomass materials can be used. The Southern Yellow Pine wood pellets used in this example have a cylindrical diameter of 7.0 mm and variable lengths from 2 mm to 15 mm. The packed bulk density of the material is 0.67 $g/cm^3$. Sorption of the most preferred oil-wax matrix onto the wood pellets averages 12.6% by weight. In a 2 inch (5.08 cm) diameter by 8 inch (20.3 cm) high support housing the volume of wood pellet packing material used was 350.9 $cm^3$ and the essential oil-wax matrix that was sorbed onto the wood pellets was equal to 33.9 g.

Design of the specific dimensions, air permeabilities and essential oil-wax mass loading per unit will vary dependent on the specific type of space to be treated (e.g., confined, semi-confined or open space), the specific application (insect control, aroma therapy, continuous or bolus treatment) as well as the duration of treatment. Mass of essential oil wax matrix to gas volume to be treated in a stationary application (fixed location) in a semi-confined or semi-enclosed space, such as an agricultural facility without mechanical ventilation varies from 0.05 $g/m^3$ to 1.0 $g/m^3$. Mass of essential oil wax matrix to gas volume to be treated in a semi-confined to confined space, such as a closet, storage room or a house without mechanical ventilation varies from 0.01 $g/m^3$ to 0.25 $g/m^3$. In an outdoor application, such as an open sided shed structure the mass of essential oil wax matrix to gas volume varies from 0.10 $g/m^3$ to 2.0 $g/m^3$.

Some embodiments include essential oil-wax matrix for the controlled release of essential oil components for insecticidal or insect repellent properties, or for aromatherapy use.

In some embodiments, the invention utilizes a wax material to control the rheology of the essential oil containing material and none of the above patents use a wax material to control the time release of the essential oil into a gas phase. In some embodiments, the essential oil-wax matrix releases essential oil at ambient temperature.

In some embodiments, the waxes may be candilla, beeswax, or carnauba wax that have melting points of 68.5° C., 66° C. and 82° C., which will not melt at body temperature. Paraffin wax may not be an effective wax to use in this instant invention as it would melt in warm summer months. Further, high wax content may prevent sufficient essential oil components from entering the ambient air over the range of ambient temperatures experienced in enclosed, semi-enclosed and outdoor spaces where flying and crawling insects may be present.

Example 1

The example perforated housing shown in FIG. 3 was used to house two different amounts of mesh material in separate housing. One unit contained a mesh with the dimensions of 20.32 cm wide by 34.39 cm long and had a total surface area of 696.8 $cm^2$, A total amount of 42.4 g of the essential oil-wax matrix was placed on the mesh, providing a 2.20 wax to mesh (w/w) ratio. The total length of line that made up the mesh material was 3,180 cm and the average line diameter was 1.5 mm. The total line surface area in the mesh used in this example is 224 $cm^2$, which resulted in an essential oil-wax loading of 0.199 $cm^3/cm^2$, resulting in an average coating thickness of 2.0 mm. The essential oil-wax matrix mass to line length loading is also calculated to be 0.013 g/cm. This unit had a mesh length to cross sectional area ratio of 5.31 $cm/cm^2$.

The second unit contained a mesh with the dimensions of 20.32 cm wide by 50.80 cm long and had a total surface area of 1032 $cm^2$. A total amount of 59.2 g of the essential oil-wax matrix was placed on the mesh, providing a 2.09 wax to mesh ratio. A total length of line was 4,663 cm and the average line diameter was 1.5 mm. The total line surface area in the mesh used in this example is 329 $cm^2$, that resulting in an essential oil-wax loading of 0.190 $cm^3/cm^2$, resulting in an average coating thickness of 1.9 mm. The essential oil-wax matrix mass to line length loading is also calculated to be 0.013 g/cm. Having a longer mesh length in this 2 inch diameter unit, than the first unit, the mesh length to cross sectional area ratio was 7.87 cm/cm$^2$.

These two units were hung from a ceiling in a center aisle of a barn with the dimensions of 36 feet (10.9 m) wide by 72 feet (21.9 m) long. The ceiling in aisle of the barn was 12 feet (3.7 m) high and the upper 4 feet (1.2 m) of the aisle walls were open to a second floor to enhance air circulation from the 1$^{st}$ floor of the barn up to a mezzanine level and then up to a hay loft. The roof of the barn has an 8 foot (2.4 in) by 8 foot large cupola with 8 double hung windows that are opened in the summer to enhance air flow through the barn. The volume of the center aisle was 10,368 ft$^3$ (293 m$^3$) and the floor area on the 1$^{st}$ floor of the barn that was open to the air is 864 ft$^2$ (80.3 m$^2$). The two units were hung approximately 1 foot (0.3 m) from the top of the 1$^{st}$ floor center aisle ceiling and each located approximately 12 feet (3.7 m) from each end of the aisle. Therefore there was a 48 foot (14.6 m) spacing between the two units. These units were placed in this barn located in Connecticut in early August 2011. The essential oil-wax matrix to volume of space in the center aisle of the barn was 0.367 g/m$^3$. The essential oil-wax matrix to floor surface area was 1.265 g/m$^2$. Generally, the two end doors of this barn are open 24 hours per day during the summer months, ensuring significant air flow though the barn. Once the units were placed in the barn, the smell of essential oils was readily recognizable throughout the center aisle of the barn and even beyond the door of barn outside of the barn in the direction to which the wind was blowing. There were no flies or mosquitoes or any other flying insects or spiders observed in the barn after the units were placed in the barn. As described in the following, two smaller units were replaced by the above two larger units. The two replaced smaller units had low air permeabilities and were beginning to not perform as well as they previously had for the prior 3 month period. During the 3 month period it was rare to see a fly, mosquito, gnat or spider in the first floor of the barn. After the 3 month period, a few flies and spiders were noticeable in this same barn after 3 months of service of the smaller units. During the entire 3.5 month period when the two smaller units were in service in the barn, there was only periodically a barely perceptible odor of essential oils detectable. Following the replacement of the two smaller units with the 2" diameter units with significantly greater air permeability, the odor of the essential oil vapors volatilizing off of the essential-oil wax matrix was continuously noticeable. It is evident from the performance of the 2 smaller units over the 3.5 month service period that there was significant repellency of flying and crawling insects in the barn despite that the essential oil odors were barely perceptible by humans.

Prior to placement of the two units in the barn, two smaller units with lower surface areas and wax content were placed in 1" (2.5 cm) diameter by 6" (15.2 cm) long PVC pipes with ⅜ inch (0.95 cm) diameter holes drilled along the sides of the units. These two smaller units were located in the same location as where the two replacement units were located. The two 1 inch (2.5 cm) diameter units were constructed similarly. One of the two 1"" (2.5 cm)×6" (15.2 cm) units contained a mesh with the dimensions of 15.24 cm wide by 24.77 cm long and had a total surface area of 377 cm$^2$. A total amount of 25.9 g of the essential oil-wax matrix was placed on the mesh, providing a 2.48 wax to mesh ratio. A total length of line was 1723 cm and the average line diameter was 1.5 mm. The total line surface area in the mesh used in this example is 122 cm$^2$, that resulting in an essential oil-wax loading of 0.220 cm$^3$/cm$^2$, resulting in an average coating thickness of 2.2 mm. The essential oil-wax matrix mass to line length loading is also calculated to be 0.015 g/cm. The two 1 inch (2.54 cm)×6 inch (15.2 cm) units photographed after 4 months of use are shown in FIG. 4. After disassembly the essential oil-wax coated mesh fabric can be seen in FIG. 5. It should be noted that this 1 inch (2.54 cm) diameter unit was packed much tighter than the 2 inch (5.08 cm) diameter units with a mesh length to cross sectional area ratio of 15.35 cm/cm$^2$. Given the tighter spiral packing or the mesh fabric in the 1 inch (2.54 cm) diameter tube, it is apparent that the wax loading on this unit resulted in complete bridging of the wax in the mesh of the fabric. This factor clearly decreases the air permeability of the essential oil-wax matrix coated mesh fabric assembly in comparison to the 2 inch (5.08 cm) diameter units. There was low air permeability in the two 1 inch (2.54 cm) diameter units with the completed bridged wax decreasing the ability of air to flow through the units. The essential oil-wax matrix to volume of space in the center aisle of the barn was 0.0.177 g/m$^3$. The essential oil-wax matrix to floor surface area was 0.645 g/m$^2$. Both of these essential oil-wax matrix loading rates are considerably lower than that of the two larger 2 inch (0.60 cm) diameter 8 inch (20.3 cm) units and also had lower air permeability than the two larger units. However, from the first week of May 2011 until Aug. 22, 2011 when these two units were located in a large barn there we no flies or other flying insects observed in the barn until the first week of August, when a few flies were observed in the barn. Generally, flies could be seen attempting to fly into the barn through the open doors (12 foot (3.7 m) by 12 foot opening) but then turning around and leaving the barn. During the entire 3.5 month period when the units were in service in the barn only periodically was a barely perceptible odor of essential oils detectable. Apparently the odor threshold for human smell of essential oils is much higher than the level at which the essential oils serve as a repellent for flies and other flying insects. It should be noted that in previous years without the solid fly repellent devices present in the barn, by mid June many spiders and spider webs are normally apparent throughout the barn. During the entire summer of 2011 with the solid fly repellent devices present in the barn it was rare to observe a spider in the barn.

Example 2

An example of a mass produced injected molded plastic mesh housing developed as part of this invention is shown in FIG. 5. This design has inner and outer diameters of 4.85 cm and 5.08 cm, respectively. The housing is 13.51 cm long. The pore openings in the housing are 3.1 mm by 3.1 mm and the entire surface area has a 30 percent open area. The bottom of the housing is solid and the top has a cap that fits on the housing with a socket type fitting. This particular housing is polypropylene, but could be made from any plastic that could be injection molded. The volume of the housing is 247.4 cm$^3$. A photograph of the essential oil-wax matrix used in this example is found in FIG. 6. The polypropylene pellets used in this example are cylindrical in shape and have a diameter of 4.12 mm, and a height of approximately 3.10 mm. The injection molded housing containing the essential oil-wax matrix coated polypropylene particles are is shown in FIG. 7. The weight of the essential oil-wax matrix coated polypropylene particles in the housing is 146.3 g and the bulk density of the coated particles in the housing is 0.59 g/cm$^3$. These essential oil-wax matrix coated pellet housing units are designed to reused. Once the desired emission of essential oil from the units is no longer achieving the desired results due to decreased essential oil fluxes to the atmosphere, the coated plastic pellets can be removed and new coated pellets can added. The used coated plastic pellets can be recoated with fresh essential oil-wax matrix and can be subsequently reused in the plastic housing. A person ordinarily skilled in the art would clearly recognize that variations of the above housing design could readily be designed with larger or smaller housing units with varying dimensions and geometries (such as spheres, cubes, rectangles, domes, and cylinders of varying dimensions as housing units for the essential oil wax matrix plastic pellet media. A person ordinarily skilled in the art would also recognize that varying pore dimensions and total porosity could be incorporated into variations on the design presented in this example.

Another preferred composition of the essential oil wax matrix was developed to contain and qualify as a minimum risk pesticide under the United States Protection Agency Federal Insecticide, Fungicide and Rodenticide Act under 40CFR 152.22 (g)(1) Appendix A. The composition of the essential oil-wax matrix with the plastic pellets is found in Table 3. In this formulation, minimum risk essential oil and essential oil extract pesticides exempted under FIFRA 25(b) were selected to formulate a composition for the purpose of creating an EPA FIFRA 25(b) exempt composition. The percent essential oils in the essential oil wax matrix is 60 percent and the percent wax is 40 percent. A person ordinarily skilled in the art would readily recognize that the percent of essential oils and waxes and the composition of the waxes can be varied to vary the rheology and mass flux release rate of the essential oils into the gas phase for varying resulting concentrations of essential oils available for repellency. The FIFRA 25(b) exempt essential oil-wax matrix coated polypropylene pellets are shown in FIG. 6.

Example 3

A test was conducted in 10 barns located in Maryland and Delaware. Eight of the barns were large housing race horses at a large training facility. In the 8 horse racing barns, 94 essential oil-wax matrix housings were installed in these 10 horse racing barns in the end of April 2012 and were monitored weekly for performance at each of the facilities. Barns tested had one of three formulations tested during these trials. Compositions tested consisted of those shown in Tables 2 and 3 Table 3 while the third composition tested was similar in composition of the EPA FIFRA 25(b) exempted formulation shown in Table 2 (with wooden pellets, instead of plastic pellets), but with a 36 percent increase in the oil wax matrix in comparison to that shown in Table 3 (also with wooden pellets). The number of essential oil-wax wood pellets units installed per barn in the 8 barn Maryland horse racing facility testing was 11.75, with a minimum of 8 units and a maximum of 19 units installed per barn. These barns were large commercial facilities, typically with high ceilings and containing 30 to 60 stalls and specialized equine care equipment. Weekly monitoring for the performance of the units in each barn was conducted before and during the two month test. After the designed two-month life of the units was over, surveys were completed by the barn managers to assess performance with respect in insect repellency. All of the representatives from each barn described a noticeable difference in the presence of flying insects in their horse barns, with an 83 out of 100 point score. The EPA FIFRA exempt formulation described in Table 3 had a 100 out of 100 point score from the 3 barns tested with this composition. The respondents that had the EPA FIFRA exempt formulations reported a 75 percent decrease in flying insects in comparison to past years. The respondents that had the composition described in Table 2 reported a 58 percent average reduction on flying insects compared to past years. The respondents that high the higher concentration of essential oil and wax in the housings only reported a 42 percent decrease in flying insects. It is believed that the reason for the lower performance in this group was due to clogging of the wood pellet porosity from the high concentration of the essential oil wax matrix in this composition. The satisfaction portion of the survey had a unanimous 100 percent satisfaction with the product.

Example 4

The essential oil wax matrix with the USE PA FIFRA 25(b) registration exempt composition described in Table 3, but without the plastic pellets, was melted then soaked into Ever Soak brand fiber pads manufactured from 80 percent recycled cellulose fiber. The pad tested had the dimensions of 12 cm long, 2.5 cm wide and 0.538 cm thick with a pad volume of 16.14 $cm^3$. The weight of the pad was 0.7416 g with a calculated density of 0.0459 $g/cm^3$. After the essential oil wax matrix was emplaced in the fiber material the final weight of the pad was 13.222 g with a calculated density of the essential oil wax matrix coated pad of 0.8254 g. The pad was placed on a clip and placed in a fume hood and allowing volatilization of the essential oils from the cellulose fiber pad material over time Periodically the pad was removed from the fume hood and weighed using an electronic balance with a sensitivity of 0.1 mg. Results of this testing are presented in FIG. 8. It can be seen that after 80 days of exposure to the advective air in the fume hood the weight of the pad slowly decreased over time. After 35 days of exposure to advective air in the fume hood a slow and linear rate weight loss was observed for the duration of the test. An identical essential oil-wax matrix coated EverSoak cellulose fiber pad was also placed on a clip in the fume hood and instead of weighing the pad, the pad was placed in a 500 mL amber glass container with a screw on Teflon septa lined lid with a hole in the plastic lid for gas phase sampling. After a 24 hour period in which the essential oil-wax matrix coated pad was allowed to equilibrate in the glass container, the gas phase was sampled and injected into a GC/MS to determine the equilibrium gas phase concentration of essential oils in the gas phase. The essential oil-wax matrix coated pad was then returned to the fume hood. The GC/MS analysis was periodically repeated to obtain a time series of gas phase equilibrium concentrations of total essential oils. The GC/MS was calibrated against standards made from a stock solution of the essential oils. The results of the GC/MS analysis was plotted over time exposed in the fume hood, as shown in FIG. 9. It can be seen that there was substantial emission of essential oils from the essential oil wax matrix coating the EverSoak polypropylene pad over a 60 day period and continuing to over a 100 day period. This essential oil-wax matrix coated polypropylene pad could be emplaced in or on clothing, equipment, structures, housing devices and other types of support materials that would allow a long term emission of essential oils into the gas phase. The purpose of the essential gas phase emissions from the essential oil-wax matrix coated polypropylene pads can be for insect control, aromatherapy and passive dispersal of fragrances into the air. The pads could be used for insect control for humans, pets, farm animals, food and vegetation. Similarly, the essential oil wax-matrix could be used to repel certain animals, birds and pests from structures, vegetation, food crops, land and other areas where it is desirable to keep certain them away.

For example, an essential oil can be included in an essential oil-wax mixture or other mixture in weight fractions ranging from about 0, 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, or 0.99 to about 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, 0.99, or 1.0.

For example, a natural wax can be included in an essential oil-wax mixture or other mixture in weight fractions ranging from about 0, 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, or 0.99 to about 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, 0.99, or 1.0.

For example, a fixed oil can be included in an essential oil-wax mixture or other mixture in weight fractions ranging from about 0, 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, or 0.99 to about 0.001, 0.003, 0.01, 0.02, 0.03, 0.04, 0.05, 0.06, 0.07, 0.08, 0.09, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.93, 0.95, 0.97, 0.98, 0.99, or 1.0.

For example, a support material can have an air permeability ranging from about $10^{-8}$ cm$^2$, $10^{-7}$ cm$^2$, $10^{-6}$ cm$^2$, $10^{-5}$ cm$^2$, $10^{-4}$ cm$^2$, $10^{-3}$ cm$^2$, $10^{-2}$ cm$^2$, $10^{-1}$ cm$^2$, or 1 cm$^2$ to about $10^{-7}$ cm$^2$, $10^{-6}$ cm$^2$, $10^{-5}$ cm$^2$, $10^{-4}$ cm$^2$, $10^{-3}$ cm$^2$, $10^{-2}$ cm$^2$, $10^{-1}$ cm$^2$, 1 cm$^2$, or 10 cm$^2$.

For example, pellets can have a spherical, cylindrical, cubic, oblong, or other form. For example, pellets can have a diameter of from about 0.1, 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 mm to about 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, 50, or 60 mm. For example, pellets can have a height of from about 0.1, 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 mm to about 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, 50, or 60 mm. For example, pellets can have a length of from about 0.1, 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 mm to about 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, 50, or 60 mm.

For example, a fabric mesh can have a fabric string of from about 0.01, 0.03, 0.1, 0.2, 0.5, 1, 1.2, 1.5, 1.8, 2, 2.5, 3, 3.5, 4, 4.5, or 5 mm to about 0.03, 0.1, 0.2, 0.5, 1, 1.2, 1.5, 1.8, 2, 2.5, 3, 3.5, 4, 4.5, 5, or 6 mm. For example, a mesh can have an open mesh spacing of from about 0.1, 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 mm to about 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, 50, or 60 mm.

For example, a mesh can have from about 1, 2, 5, 10, 15, 20, 25, 30, 35, 40, 45, 50, 55, 60, 65, 70, 75, 80, 85, 90, 95, 98, or 99 percent open area to about 2, 5, 10, 15, 20, 25, 30, 35, 40, 45, 50, 55, 60, 65, 70, 75, 80, 85, 90, 95, 98, 99, or 99.5 percent open area. For example, a cylindrical mesh can have an inner diameter of from about 0.5, 1, 2, 3, 4, 5, 6, 7, 8, 9, or 10 cm to about 1, 2, 3, 4, 5, 6, 7, 8, 9, 10, or 15 cm. For example, a cylindrical mesh can have an outer diameter of from about 0.5, 1, 2, 3, 4, 5, 6, 7, 8, 9, or 10 cm to about 1, 2, 3, 4, 5, 6, 7, 8, 9, 10, or 15 cm. For example, a cylindrical mesh can have a length of from about 0.5, 1, 2, 3, 4, 5, 6, 7, 8, 9, 10, 12, 15, 18, 20, 25, 30, 35, 40, 45, or 50 cm to about 1, 2, 3, 4, 5, 6, 7, 8, 9, 10, 12, 15, 18, 20, 25, 30, 35, 40, 45, 50 or 60 cm. For example, a mesh can have an opening with a diameter, diagonal length, or length across of from about 0.1, 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, or 50 mm to about 0.2, 0.5, 1, 1.5, 2, 2.5, 3, 3.5, 4, 4.5, 5, 5.5, 6, 6.5, 7, 7.5, 8, 8.5, 9, 9.5, 10, 12, 15, 20, 25, 30, 35, 40, 45, 50, or 60 mm.

For example, a pad, fiber pad, or cellulose fiber can have a thickness of from about 0.01, 0.02, 0.05, 0.1, 0.15, 0.2, 0.25, 0.3, 0.35, 0.4, 0.45, 0.5, 0.55, 0.6, 0.65, 0.7, 0.75, 0.8, 0.9, 1, 1.5, 2, 2.5, 3, 3.5, 4, 4.5, or 5 cm to about 0.02, 0.05, 0.1, 0.15, 0.2, 0.25, 0.3, 0.35, 0.4, 0.45, 0.5, 0.55, 0.6, 0.65, 0.7, 0.75, 0.8, 0.9, 1, 1.5, 2, 2.5, 3, 3.5, 4, 4.5, 5, or 10 cm.

For example, an essential oil-wax mixture can have from about 1, 2, 5, 10, 15, 20, 25, 30, 35, 40, 45, 50, 55, 60, 65, 70, 75, 80, 85, 90, 95, 98, or 99 percent by weight essential oils to about 2, 5, 10, 15, 20, 25, 30, 35, 40, 45, 50, 55, 60, 65, 70, 75, 80, 85, 90, 95, 98, 99, or 99.5 percent by weight essential oils. For example, an essential oil-wax mixture can have from about 1, 2, 5, 10, 15, 20, 25, 30, 35, 40, 45, 50, 55, 60, 65, 70, 75, 80, 85, 90, 95, 98, or 99 percent by weight waxes to about 2, 5, 10, 15, 20, 25, 30, 35, 40, 45, 50, 55, 60, 65, 70, 75, 80, 85, 90, 95, 98, 99, or 99.5 percent by weight waxes.

For example, a pellet can have an overall bulk density of from about 0.1, 0.2, 0.3, 0.4, 0.5, 0.55, 0.6, 0.65, 0.7, 0.75, 0.8, 0.85, 0.9, or 0.95 g/cm$^3$ to about 0.2, 0.3, 0.4, 0.5, 0.55, 0.6, 0.65, 0.7, 0.75, 0.8, 0.85, 0.9, or 0.95 g/cm$^3$. For example, a pellet can have an essential oil-wax loading (weight of wax/weight of pellets) of from about 0.5, 1, 2, 5, 10, 12, 15, 18, 20, 25, 30, 35, 40, 45, 50, 55, 60, 65, 70, 75, 80, 85, 90, or 95 percent by weight to about 1, 2, 5, 10, 12, 15, 18, 20, 25, 30, 35, 40, 45, 50, 55, 60, 65, 70, 75, 80, 85, 90, or 98 percent by weight.

For example, a fabric mesh can have an essential oil-wax loading on the fabric mesh of from about 0.01, 0.02, 0.03, 0.04, 0.05, 0.6, 0.08, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.2, 1.5, 2, 2.5, 3, 3.5, 4, 4.5, 5, 5.5, 6, 6.5, 7, 7.5, 8, 8.5, 9, 9.5, 10, 12, 15, or 20 cm$^3$/cm$^2$ to about 0.02, 0.03, 0.04, 0.05, 0.6, 0.08, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.2, 1.5, 2, 2.5, 3, 3.5, 4, 4.5, 5, 5.5, 6, 6.5, 7, 7.5, 8, 8.5, 9, 9.5, 10, 12, 15, 20, or 30 cm$^3$/cm$^2$. For example, a fabric mesh can have an essential oil-wax thickness on the fabric mesh of from about 0.01, 0.02, 0.03, 0.04, 0.05, 0.6, 0.08, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.2, 1.5, 2, 2.5, 3, 3.5, 4, 4.5, 5, 5.5, 6, 6.5, 7, 7.5, 8, 8.5, 9, 9.5, 10, 12, 15, or 20 mm to about 0.02, 0.03, 0.04, 0.05, 0.6, 0.08, 0.1, 0.12, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.2, 1.5, 2, 2.5, 3, 3.5, 4, 4.5, 5, 5.5, 6, 6.5, 7, 7.5, 8, 8.5, 9, 9.5, 10, 12, 15, 20, or 30 mm.

For example, the value of the mass of an essential oil-wax mixture to gas volume to be treated can be in a range of from about 0.001, 0.003, 0.01, 0.02, 0.05, 0.1, 0.2, 0.3, 0.4, 0.5, 0.6, 0.7, 0.8, 0.9, 1, 1.2, 1.5, 2, 2.5, 3, 3.5, 4, 4.5, 5, 7, 10, 12, 15, 20, 25, 30, 40, 50, or 70 g/m$^3$ to about 0.003, 0.01, 0.02, 0.05, 0.1, 0.2, 0.3, 0.4, 0.5, 0.6, 0.7, 0.8, 0.9, 1, 1.2, 1.5, 2, 2.5, 3, 3.5, 4, 4.5, 5, 7, 10, 12, 15, 20, 25, 30, 40, 50, 70, or 100 g/m$^3$.

For example, the pore size of a gas permeable membrane can be in a range of from about 0.01, 0.03, 0.1, 0.2, 0.5, 1, 1.5, 2, 2.5, 3, 4, 5, 7, 10, 15, 20, 25, 30, 40, 50, 60, 70, 80, 90, 100, 110, 120, 150, 200, 250, 300, 400, 500, or 700 µm to about 0.03, 0.1, 0.2, 0.5, 1, 1.5, 2, 2.5, 3, 4, 5, 7, 10, 15, 20, 25, 30, 40, 50, 60, 70, 80, 90, 100, 110, 120, 150, 200, 250, 300, 400, 500, 700, or 1000 µm.

In an embodiment according to the invention, a composition is effective at repelling insects, arachnids and other arthropods by the slow release volatilization of essential oils into a gas phase. For example, the composition can include one or more essential oils or their extracts, one or more fixed oils, one or more natural waxes, a support material onto which a matrix of the essential oil and the natural wax is solidified, and/or a housing or container that retains the essential oil-wax matrix on the support material with sufficient air permeability or diffusivity to allow volatilization, mass transfer and diffusion of the volatile fraction of the essential oil from the essential oil-wax matrix.

All documents cited herein are hereby incorporated by reference in their entirety. This application claims the benefit of U.S. Provisional Application No. 61/552,488, filed Oct. 28, 2011, which is hereby incorporated by reference in its entirety.

Although the foregoing invention has been described in some detail for purposes of clarity of understanding, those skilled in the art will appreciate that various adaptations and modifications of the just described preferred embodiments can be configured without departing from the scope and spirit of the invention. The described embodiments should be taken as illustrative and not restrictive, and the invention should not be limited to the details given herein but should be defined by the following claims and their full scope of equivalents.

REFERENCES

Food Quality Protection Act of 1996. P.L. 104-170

Manniche, L. (1989) An Ancient Egyptian Herbal. British Museum Publications, London, England.

Tisserand. R., and Balacs, T. (1995) *Essential Oil Safety, A Guide for Health Care Professionals*. Churchill Livingstone, Elsevier. Edinburgh.

Faith, Carole (2002). Essential Oils for Horses. Trafalgar Square Publishing, Vermont, USA. 224 pp.

Baser, K. H. C., and Buchbauer, G. (2010) *Handbook of Essential Oils: Science, Technology, and Applications*, CRC Press/Talyor Francis.

U.S. Pat. No. 4,961,929, Gurvich, et al. "Process of repelling dogs and dog repellent material," Oct. 9, 1990.

U.S. Pat. No. 4,735,803, Katz, et al. "Repelling animals with compositions comprising lemon oil and alpha-terpinyl methyl ether," Apr. 5, 1988.

U.S. Pat. No. 4,847,292, Katz et al., Repelling animals with compositions comprising citronellyl nitrile, citronellol, alpha-terpinyl methyl ether and lemon oil, Jul. 11, 1989.

Kambouzia, K. J., Negahban, M., and Moharramipour, S. (2009) Fumigant toxicity of *Eucalyptus leucoxylon* Against Stored Prodcut Insects. *American-Eurasian Journal of Sustainable Agriculture*. 3(2):229-233.

Liu, Z. L., Chu, S. S., and Jiang, G. H. (2010) Insecticidal Activity and Composition of Essential Oil of *Oxtericum sieboldii* (Apiaceae) Against *Sitiphilus zeamais* and *Tribolium castaneum*, Academy of Chemistry Globe Publications, Records of Natural Products, 5:2, 74-81.

Mareggiani, G., Russo, S., and Rocca, M. (2008) Eucalyptus globules (Mirtaceae) Essential oil: Efficiay against *Aphis gosypii* (*Hemiptera*:Aphididae) and Agricultural Pest. Rev. Latinoameri. Quim. 36/1.

Clemente, S. V., G. Mareggiani, A. Broussalis, and Ferraro, G. 2007. Activated insecticida de 1,8-cineol sobre mosca de los frutos, *Ceratitis capitata* Wied. (*Diptera*: Tephritidae). Dominguezia 23:29-34.

Katooli, N., Maghsodlo, R., and Razavi, S. E. (2011) Evaluation of Eucalyptus Essential Oil against Some Plant pathogenic Fungi. Journal of Plant Breeding and Crop Science, 3(2) 41-43.

U.S. Pat. No. 5,705,175, Johnson. "Non Aqueous Controlled Release Insect Repellent and Insecticide Gels" Jan. 6, 1998.

U.S. Pat. No. 4,469,613, Munteanum M. A., "Detergent Bar Containing Poly(epsilon caprolactone) and Aromatizing Agent" Sep. 4, 1984

U.S. Pat. No. 4,812,309, Ong, C. J. "Gel Insecticidal Compositions", Mar. 14, 1989.

U.S. Pat. No. 4,906,488, Pera, I. E., "Modification of Permeant", Mar. 6, 1990.

U.S. Pat. No. 5,208,038, Gressani, T. M., and Klein, W. L. "Coacervated Highly Absorptive Polymers", May 4, 1990.

U.S. Pat. No. 5,372,817, Locke, J. C., Walter, J. F., and Larew, H. G., Insecticidal Compositions Derived from Neem Oil and Neem Wax Fractions. Dec. 13, 1994.

U.S. Pat. No. 5,183,690, Carr, M. E., Doane, W. M., Wing, R. E., and Bagley, E. B. "Starch Encapsulation of Biologically Active Agents by a Continuous Process", Feb. 2, 1993.

U.S. Pat. No. 4,587,129, Kliment, C. K., "Hydrophilic Gels Containing High Amounts of Fragrance", May 6, 1986.

U.S. Pat. No. 6,015,570, Tucci, R. J., and Dry, N. M., "Slow-Release Insect-Repellent Compositions and Uses", Jan. 18, 2000.

U.S. Pat. No. 6,180,127 B1, Calton, G. J., Siemer, S. R., and Wood, L. L., "Slow Release Insect Repellents", Jan. 30, 2001

U.S. Pat. No. 6,306,415 B1, Reifenrath, W. G, "Natural Insect and Arthropod Repellent", Oct. 23, 2001.

U.S. Pat. No. 6,936,269 B2, Robinson, V. S., "Insect Repellent Substrate for Headwear", Aug. 30, 2005

U.S. Pat. No. 7,455,852 B2, Birch, R. A., and Helwig, H., "Insect Repellents'", Nov. 25, 2008.

U.S. Pat. No. 7,780,972 B2, Hurwitz, M. M., Pet Collar with Replaceable Element, Aug. 24, 2010.

U.S. Pat. No. 7,846,463 B2, Johal, S., "Pest Control Composition and Method, Dec. 7, 2010.

U.S. Pat. No. 7,858,127 B2, Overman, G. R., "Method for Admixing Plant Essential Oils to Coatings for the Purpose of Repelling Insects", Dec. 28, 2010.

TABLE 1

Major Essential Oils and Constituents That May be used This Invention

| Plant | Constituents and Concentrations in the Oil |
|---|---|
| Bergamot (*Citrus bergamia*) | Linalyl acetate 36-45%, Limonene (28-32%), Linalool (11-22%), Bergapten (0.3-0.4%) |
| Cedarwood (*Cedrus atlantica* and *Juniperus viginiana*) | Cedrol, Cedrene |
| Citronella (*Cymbopogon winterianus* and *Cymbopogon nardus*) | Citral, Citronellol, Eugenol, Geraniol and Limonene |
| Eucalyptus (*Eucalyptus globulus*, *Eucalyptus citriodora*) | Eucalptol (cineole) 75%, piperitone, phellandrene, citral, methyl cinnamate and geranyl acetate |
| Gernaium (*Pelargonium graveolens*) | Citronellol, Geraniol |
| Lavender (*Lavandula angustifolia*) | Linalool, Linalyl acetate |
| Lemon (*Citrus limonum*) | Limonene 70%, Furanocoumarins 2% |
| Lemon Balm (*Melissa officinalis*) | Carophyllene 4-6%, Citral (35-55%), Gernial, Neral, Citronellal (4-39%), Linalool |
| Lemongrass (*Cymbopogon flexuosus* and *Cymbopogon citrat*us) | Citral 70%, Limonene 5% |
| Litsea cubeba (*Litsea cubeba*) | Citral (75%), Cineole, Citronellal, Citronellol, Geraniol, Linalyl acetate, Limonene (5%), Linalool |
| Peppermint (*Mentha piperita*) | I-Menthol (40-50%), Menthonen (19%), d-Pulegone (0.1-2%) |
| Neem (*Azadirachta indica*) | Azadirachtin, salinnin, vepol, meliantriol, campesterol, beta-sitosterol, stigmasterol |
| Rosemary (*Rosmarinus officnialis*) | alpha-pinene (10-125), Camphor (10-13%), Cineole (40-44%) |
| Sandalwood (*Santalum spicatum*) | α-Santalol (50-60%), β-Santalol (20-25%) |
| Tea Tree (*Melaleuca alternifolia*) | Terpinen-4-ol (30-48%), ?-Terpinene (10-28%), α-Terpinene (5-13%), Cineole (0-15%), α-Terpinolene (1.5-5%), α-Terpineol (1.5-8%), α-Pinene (1-6%), p-cymene (0.5-8%) |

TABLE 2

Most Preferred Essential Oil Wax Composition

| Component | Weight Fraction |
|---|---|
| *Eucalyptus citriodora* | 0.276 |
| d-Limonene | 0.034 |
| *Lavandula angustifolia* | 0.069 |
| *Cymbopogon winterianus* | 0.069 |
| *Mentha piperita* | 0.034 |
| *Melaleuca alternifolia* | 0.034 |
| *Azadirachta indica* | 0.138 |
| *Cymbopogon flexuosus* | 0.069 |
| Candilla Wax | 0.276 |
| TOTAL | 1.000 |

TABLE 3

Composition of EPA FIFRA Section 25(b) Registration Exempt Essential Oil Wax Matrix with Support Plastic Pellets

| Component | Weight (g) |
|---|---|
| Cedar Oil - *Cedrus deodora* | 2.2 |
| Rosemary oil - *Rosmarinus Officinalis* | 6.8 |
| Clove Oil - *Syzgium aromaticum* | 4.5 |
| Citronella Oil - *Cymbopogon winterianus* | 4.5 |
| Peppermint Oil - *Mentha piperita* | 2.2 |
| Cinnamon Oil - *Cinnamomum zeylanicum* | 2.2 |
| Lemongrass Oil - *Cymbopogon flexuosus* | 1.5 |
| Geraniol | 1.5 |
| Linseed Oil | 2.3 |
| Beeswax | 13.2 |
| Carnauba wax | 4.6 |
| TOTAL Chemicals | 45.4 |
| Plastic Pellets in Wax | 101.0 |
| Total Plastic pellets and EcoPellent oil wax | 146.3 |

The invention claimed is:

1. A composition that provides the volatilization of essential oils into a gas phase, comprising:
   a mixture comprising one or more essential oils or their extracts dissolved within one or more waxes to form a matrix;
   a support material onto which the matrix of the essential oil and the wax is solidified; and
   a housing or container that retains the essential oil-wax matrix on the support material with sufficient air permeability or diffusivity to allow volatilization, mass transfer and diffusion of the volatile fraction of the essential oil from the essential oil-wax matrix, wherein the percentage of essential oil in the matrix is greater than 50% by weight.

2. The composition of claim 1, wherein the one or more essential oils are selected from the group consisting of Bergamot, Cajeput, Catnip, Cedar, Cinnamon, Citronella, Clove, Eugenol, Eucalyptus, Eucalyptus Lemon, Eucalyptus Peppermint, Garlic, Geraniol, Geranium, Lavender, Lemon, Lemon Balm, Lemongrass, d-Limonene, *Litsea cubeba*, Long Leaf Pine, Neem, Orange, Patchouli, Peppermint, Rosemary, Sandalwood, Scotch Pine, Tea Tree, Thyme, Virginia Cedarwood, and combinations.

3. The composition of claim 1, wherein the one or more essential oils comprise *Cedrus deodora, Rosmarinus officinalis, Syzgium aromaticum, Cymbopogon winterianus, Mentha piperita, Cinnamomum zeylanicum, Cymbopogon flexuosus*, and Geraniol extract.

4. The composition of claim 1, wherein the one or more essential oils comprise *Eucalyptus citriodora*, d-Limonene, *Lavandula angustifolia, Cymbopogon winterianus, Mentha piperita, Melaleuca alternifolia, Azadirachta indica*, and *Cymbopogon flexuosus*.

5. The composition of claim 1, further comprising a fixed oil with insect repellent properties.

6. The composition of claim 5, wherein the fixed oil is selected from the group consisting of andiroba oil, karanja oil, sangre de grado oil, neem oil, linseed oil, and combinations.

7. The composition of claim 1, wherein the one or more waxes are selected from the group consisting of candilla, carnauba, beeswax, and combinations.

8. The composition of claim 1, wherein the weight fractions of the essential oil-wax matrix are *Cedrus deodora* (about 0.048), *Rosmarinus officinalis* (about 0.150), *Syzgium aromatium* (about 0.100), *Cymbopogon winterianus* (about 0.100), *Mentha piperita* (about 0.048), *Cinnamomum zeylanicum* (about 0.048), *Cymbopogon flexuosus* (about 0.032), Geraniol extract (about 0.032), Linseed oil (about 0.050), Beeswax (about 0.291), and Carnauba wax (about 0.101).

9. The composition of claim 1, wherein the preferred weight fractions of the essential oil-wax matrix are *Eucalyptus citriodora* (about 0.276), d-Limonene (about 0.034), *Lavandula angustifolia* (about 0.069), *Cymbopogon winterianus* (about 0.069), *Mentha piperita* (about 0.034), *Melaleuca alternifolia* (about 0.034), *Azadirachta indica* (about 0.138), *Cymbopogon flexuosus* (about 0.069), and Candilla wax (about 0.276).

10. The composition of claim 1, wherein the support material is selected from the group consisting of wood, wood pellets, bamboo pellets, mesh, foam, sponge-like materials, metals, bamboo fibers, wood fibers, strings, ropes, cloths, porous plastic material, solid plastic material, fibrous plastic material, plastic mesh material, pumice, gravel, sand, stone, clay, zeolites, resins, microporous materials, mesoporous materials, granular activated carbon, solid plastic pellets, fabric mesh, and combinations.

11. The composition of claim 10, wherein the support material is selected from the group consisting of solid plastic pellets, wood pellets, fabric mesh, and combinations.

12. The composition of claim 10, wherein the support material with the solidified essential oil-wax mixture has an air permeability ranging from about $10^{-1}$ cm$^2$ to $10^{-7}$ cm$^2$.

13. The composition of claim 10, wherein the support material is solid plastic pellets, and wherein the solid plastic pellets are cylindrical in shape and have a diameter of about 4.12 mm and a height of about 3.10 mm.

14. A composition of claim 1, wherein the housing or container comprises a porous material.

15. A composition of claim 14, wherein the housing or container is selected from the group consisting of a cylindrical plastic mesh, a cylindrical PVC slotted pipe, a cylindrical PVC perforated pipe, a porous plastic pipe, a metal container with a porous plastic top, a plastic container with a porous plastic top, a metal container with a gas permeable membrane top, a plastic container with a gas permeable membrane top, a plastic cylinder, a wood cylinder, a gas permeable membrane material, and combinations.

16. A composition of claim 15, wherein the housing or container is a cylindrical plastic mesh with an about 30 percent open area, inner and outer diameters of about 4.85 cm and about 5.08 cm, respectively, and length of about 13.51 cm that is injection molded from polypropylene with openings having a dimension of about 3.15 mm by about 4.00 mm, with a removal socket fitting top with a hanger hook integrated in the removal polypropylene top.

17. A composition of claim 1, wherein the support material is a cellulose fiber pad with a thickness of about 0.538 cm.

18. The composition of claim 10, wherein the support material is solid plastic pellets, wherein the plastic pellets are coated with the essential oil-wax mixture, wherein the essential oil-wax mixture has about 60 percent by weight essential oils and 40 percent by weight waxes, to achieve an overall bulk density of the essential oil-wax mixture plastic pellet mixture of from about 0.4 g/cm$^3$ to about 0.591 g/cm$^3$.

19. The composition of claim 1, wherein the volatilization of essential oils into a gas phase is without pumping, dispersion, or combustion.

20. The composition of claim 1, wherein the volatilization of essential oils into a gas phase is effective at repelling insects, arachnids and other arthropods.

21. The composition of claim 1, wherein the volatilization of essential oils into a gas phase in the presence of an individual or animal provides aromatherapy and aromachology health benefits to the individual or animal.

22. The composition of claim 1, wherein the essential oil-wax loading (wax/oil: support weight ratio) is within the range of 1:200 and 19:20.

23. The composition of claim 1, wherein the essential oil-wax loading (wax/oil: support weight ratio) is within the range of 1:4 and 13:20.

24. The composition of claim 1, wherein the essential oil-wax loading (wax/oil: support weight ratio) is within the range of 7:20 and 11:20.

25. The composition of claim 1, wherein the essential oil-wax loading (wax/oil: support weight ratio) is approximately 9:20.

26. The composition of claim 1, wherein the matrix is formed by heating the mixture above the melting point of the wax, thereby liquefying the mixture.

27. A composition that provides the volatilization of essential oils into a gas phase, comprising:
  a mixture comprising one or more essential oils or their extracts dissolved within one or more waxes to form a matrix;
  a support material onto which the matrix of the essential oil and the wax is solidified; and
  a housing or container that retains the essential oil-wax matrix on the support material with sufficient air permeability or diffusivity to allow volatilization, mass transfer and diffusion of the volatile fraction of the essential oil from the essential oil-wax matrix, wherein the support material with the solidified essential oil-wax mixture has a gas permeability of at least $10^{-7}$ cm$^2$, and the percentage of essential oil in the matrix is above 50 percent by weight.

28. The composition of claim 27, wherein the percentage of essential oil in the matrix is approximately 60% by weight.

29. The composition of claim 27, wherein the mixture comprises all of the oils in the group consisting of *Cedrus deodora, Rosmarinus officinalis, Syzgium aromaticum, Cymbopogon winterianus, Mentha piperita, Cinnamomum zeylanicum, Cymbopogon flexuosus*, and Geraniol extract.

30. The composition of claim 29, wherein the wax comprises a combination of beeswax and carnauba wax.

31. A composition that provides the volatilization of essential oils into a gas phase, comprising:
  a mixture comprising a plurality of essential oils or their extracts selected from the group consisting of *Cedrus deodora, Rosmarinus officinalis, Syzgium aromaticum, Cymbopogon winterianus, Mentha piperita, Cinnamomum zeylanicum, Cymbopogon flexuosus*, and Geraniol extract dissolved within one or more waxes to form a matrix;
  a support material onto which the matrix of the essential oil and the wax is solidified; and
  a housing or container that retains the essential oil-wax matrix on the support material with sufficient air permeability or diffusivity to allow volatilization, mass transfer and diffusion of the volatile fraction of the essential oil from the essential oil-wax matrix, wherein the percentage of essential oil in the matrix is greater than 50% by weight.

32. The composition of claim 31, wherein the percentage of essential oil in the matrix is approximately 60% by weight.

33. The composition of claim 31, wherein the wax comprises a combination of beeswax and carnauba wax.

* * * * *